United States Patent [19]

Motoyuki et al.

[11] Patent Number: 6,018,086
[45] Date of Patent: Jan. 25, 2000

[54] PROCESS FOR PREPARING 2,6-DIALKYLNAPHTHALENE

[75] Inventors: Masahiro Motoyuki, Osaka; Koji Yamamoto, Kobe, both of Japan; Ajit Vishwanath Sapre, Moorestown; John Paul Mc Williams, Woodbury, both of N.J.; Susan Patricia Donnelly, Kingwood, Tex.

[73] Assignees: Kabushiki Kaisha Kobe Seiko Sho, Kobe, Japan; Mobil Oil Corporation, Fairfax, Va.

[21] Appl. No.: 08/948,299

[22] Filed: Oct. 10, 1997

[51] Int. Cl.$^7$ .............................. C07C 1/00; C07C 2/68; C07C 5/22; C07C 4/12

[52] U.S. Cl. .................... 585/323; 585/313; 585/314; 585/315; 585/316; 585/320; 585/449; 585/467; 585/475; 585/481; 585/483

[58] Field of Search .................... 585/310, 312, 585/313, 314, 315, 316, 319, 320, 323, 494, 450, 475, 467, 477, 481, 483

[56] References Cited

U.S. PATENT DOCUMENTS

| 4,950,824 | 8/1990 | Shiroto et al. ................... 585/320 |
| 5,292,934 | 3/1994 | Sikkenga et al. ................. 562/413 |

FOREIGN PATENT DOCUMENTS

WO90/03961  4/1990  WIPO .

*Primary Examiner*—Walter D. Griffin
*Assistant Examiner*—Thuan D. Dang
*Attorney, Agent, or Firm*—Oblon, Spivak, McClelland, Maier & Neustadt, P.C.

[57] ABSTRACT

The present invention relates to a process of preparing dialkylnaphthylenes and polyalkylenenaphthyleneates.

27 Claims, 13 Drawing Sheets

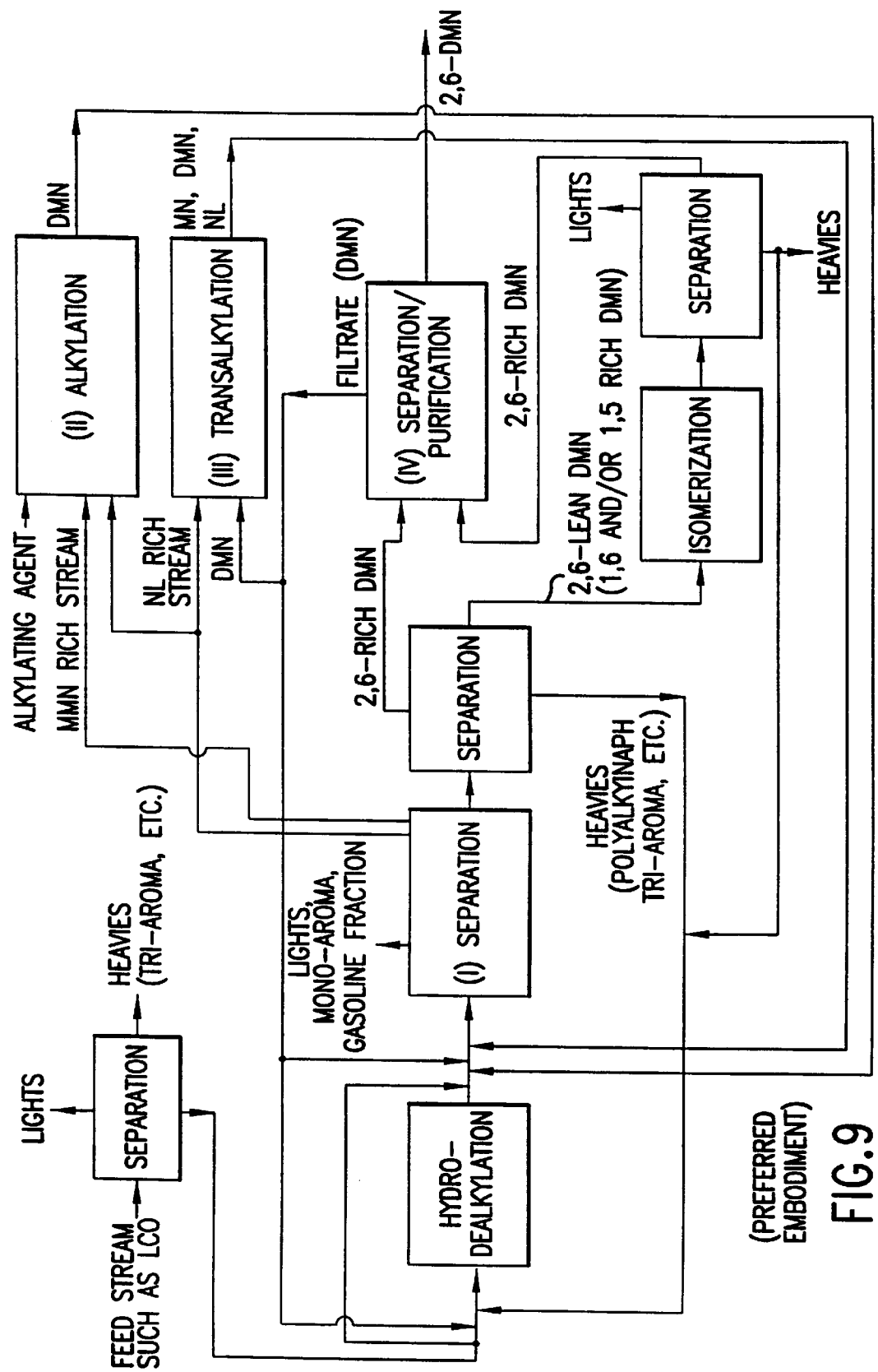
FIG. 9 (PREFERRED EMBODIMENT)

PROCESS FOR PREPARING 2,6-DIALKYLNAPHTHALENE

BACKGROUND OF THE INVENTION

1. Field of the Invention

The present invention relates to a process for producing and obtaining 2,6-dialkylnaphthalene (DAN), in particular 2,6-dimethylnaphthylene (2,6-DMN) from a mixture which contains at least one of dialkylnaphthalenes, monoalylnaphthalenes or naphthalene.

2. Discussion of the Background

The compound 2,6-DMN is used as a precursor of 2,6-naphthalene dicarboxylic acid in the manufacture of high performance polyester resins such as polyethylene naphthalate polymer (PEN) or polybutyrene naphthalate polymer (PBN), because 2,6-DMN is easily oxidized to 2,6-naphthalene dicarboxylic acid compared with other precursors such as 2,6-diisopropylnaphthalene or 2-methyl-6-isobutyrylnaphthalenes. There have been many expected PEN's applications to film and bottle uses, such as long time recording type video film, Advanced Photo System, hot fill containers, refillable bottles and tire codes because of its good physical properties in strength, thermal resistance and gas barrier property. Expected PBN's main applications are for electronics, insulators and car parts. However, PEN and PBN have heretofore been too expensive to expand its market cleanly because of few effective processes for the 2,6-DMN commercialization.

There have been many proposals concerning the process for preparing the 2,6-DMN.

U.S. Pat. No. 4,795,847 (Weitkamp et al.) describes a process for the preparation of 2,6-dialkylnaphthalene by alkylating naphthalene or 2-alkyl-naphthalene with an alkylating agent in the presence of a zeolite (specially ZSM-5) as a catalyst.

U.S. Pat. No. 5,001,295 (Angevine et al) describes a process for preparing DMN by using 2-monomethylnaphthalene (MMN) and naphthalene as a feedstock and a synthetic zeolite (MCM-22) as a catalyst, and it shows MCM-22 is more effective than ZSM-5 in alkylation of 2-MMN and naphthalene.

However these methods provide only unit operation (i.e batch) for alkylation of 2-MMN, which is an expensive feedstock and is not commercially available in a large amounts.

U.S. Pat. Nos. 4,990,717 (Sikkenga) and 5,073,670 (Sikkenga et al.) describes a multi-step process to produce 2,6-DMN from o-xylene and butadiene, which consists of;

1) preparation of 5-(o-tolyl)-pentene-2 (OTP) by alkenylation of o-xylene with butadiene in a presence of catalyst such as an alkali metal catalyst;

2) preparation of 1,5-dimethyltetralin (1,5-DMT) by cyclization of OTP in a presence of catalyst such as platinum and copper on an ultra stable zeolite catalyst;

3) preparation of 1,5-dimethylnaphthalene (1,5-DMN) by dehydrogenation of 1,5-DMT in a presence of catalyst such as platinum and rhenium and gamma alumina; and 4) preparation of DMN mixture which is rich in the desirable 2,6-DMN, 1,6-DMN and 1,5-DMN by isomerization of 1,5-DMN in a presence of catalyst such as a beta-zeolite catalyst.

If a 2,6-DMN separation from DMN mixture were combined with the above multi-steps, a complete process to produce purified 2,6-DMN could be provided.

As multiples steps makes a process plant complicate and in a high cost, it is hard to say that the prior art provides or a commercial process for an economical preparation of purified 2,6-DMN.

Furthermore, it is very difficult to separate 2,6-DMN from other isomers by conventional separation methods such as distillation and cooling crystallization because;

1) There are very small differences in boiling points of DMN isomers, especially the difference between 2,6-DMN and 2,7-DMN is only 0.3° C., where it is nearly impossible to separate 2,6-DMN by distillation.

2) The cooling of DMN isomer mixture solution of 2,6-DMN purification formes a precipitate of very fine 2,6-DMN crystals in suspension, where separation of the 2,6-DMN is extremely difficult.

Koide et al U.S. Pat. No. 4,992,619 reports a method of separating a methyl derivative of naphthalene from a mixture material in a high purity, by crystallization under a pressure.

Moritoki et al U.S. Pat. No. 4,784,766 reports a pressure crystallization apparatus.

Accordingly, method of commercially preparing dialkylnaphthalenes are sought.

SUMMARY OF THE INVENTION

According to one embodiment of the invention is a method of preparing 2,6-dialkylnaphthalene.

According to another embodiment of the present invention is a method of preparaing 2,6-dimethylnaphthylene.

According to another embodiment of the present invention is a method of preparing a polyester resin.

These and other objects of the present invention are made possible by a method of producing 2,6-dialkylnaphthalene from a feedstock which contains at least one component selected from the group consisting of dialkynaphthalene isomers, monoalkylnaphthalene isomers and naphthalene comprising the following steps:

I. separating a feedstock into a naphthalene, monoalkynaphthalene, dialkylnaphthalene fractions:

II. separating and purifying 2,6-dialkylnaphthalene from said dialkylnaphthlane fraction of step I;

III. alkylating said monoalkylnaphthalene fraction of step I with an alkylating agent to produce dialkylnaphthalene;

IV. transalkylating said naphthalene fraction of step I and a dialkylnaphthalene fraction, after 2,6-dialkylnaphthalene is separated therefrom in step II, to produce monoalkylnaphthalene, and isomers of dialkylnaphthalene.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIGS. 3, 4, 5, 6, 7, 8 and 9 illustrate separation, purification and reaction schemes according to preferred embodiments of the present invention.

DESCRIPTION OF THE PREFERRED EMBODIMENTS

Figure 1:
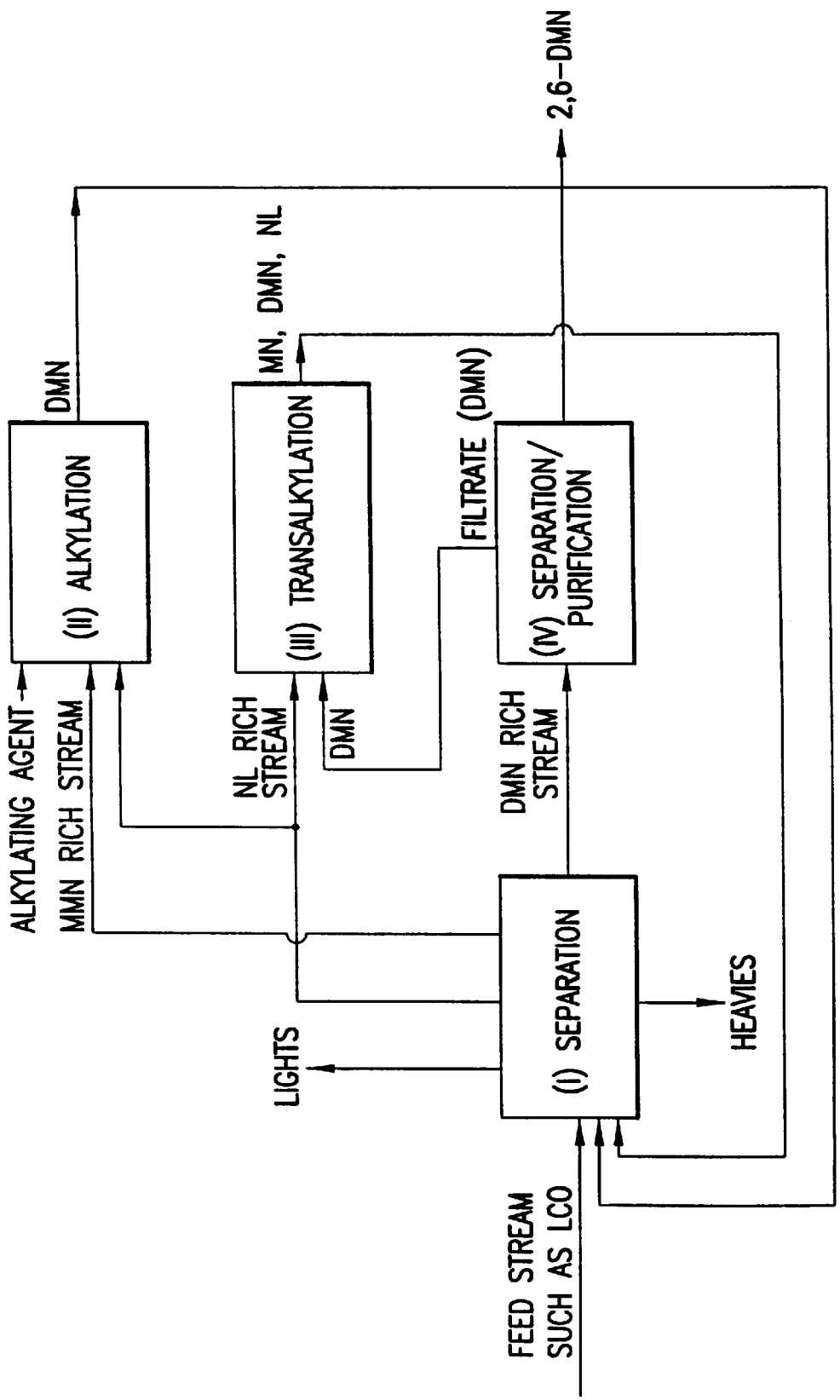
FIG. 1, illustrates a separation, purification and reaction scheme according to the present invention.
Figure 2:
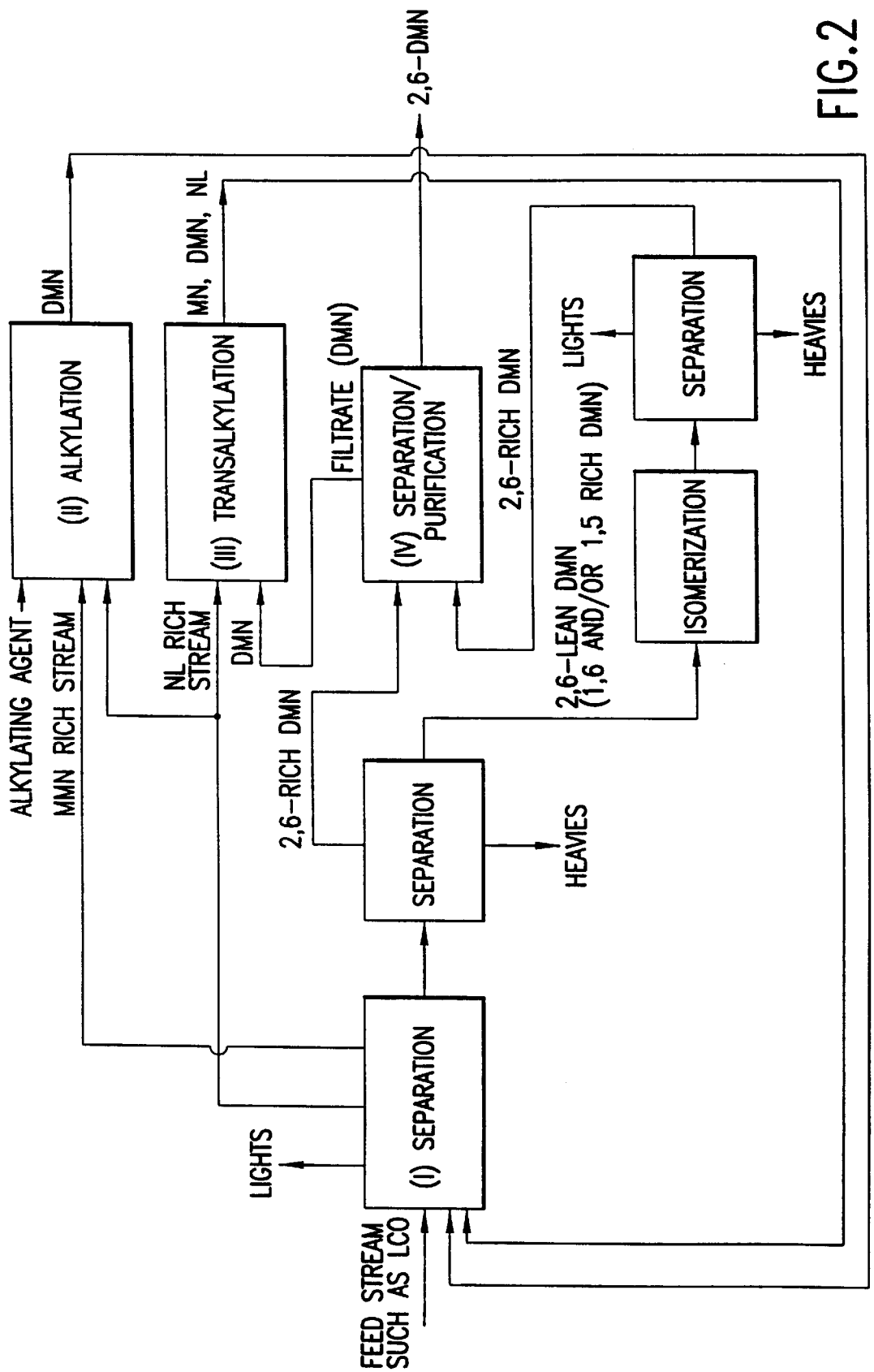
FIG. 2, illustrates a separation, purification and reaction scheme wherein a dialkylnaphthalene fraction is enriched in 2,6-dialkylnaphthalene, according to the present invention.
Figure 3A:
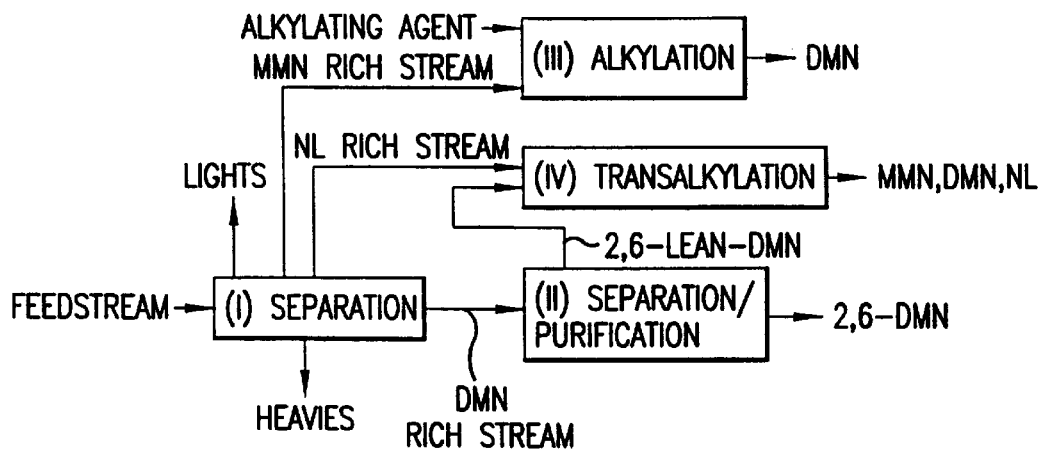
Figure 3B:
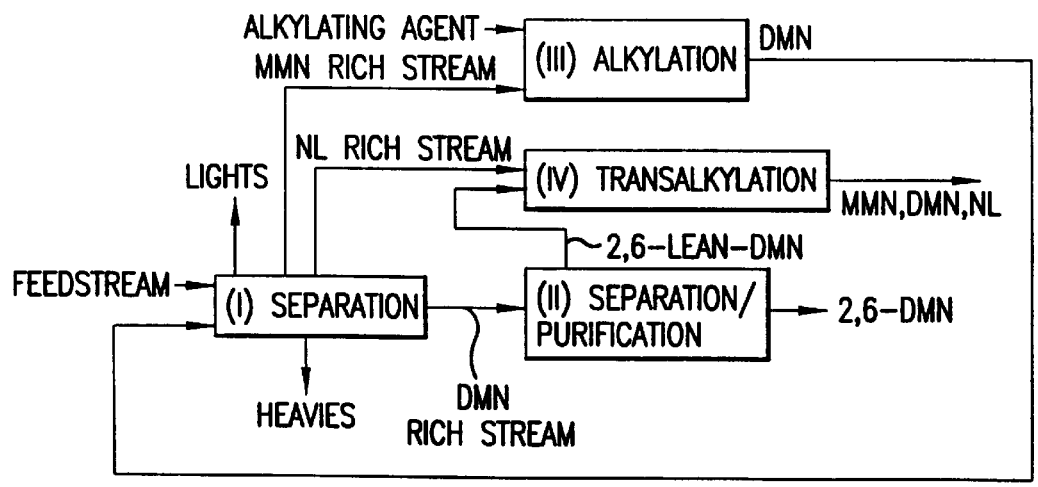
Figure 3C:
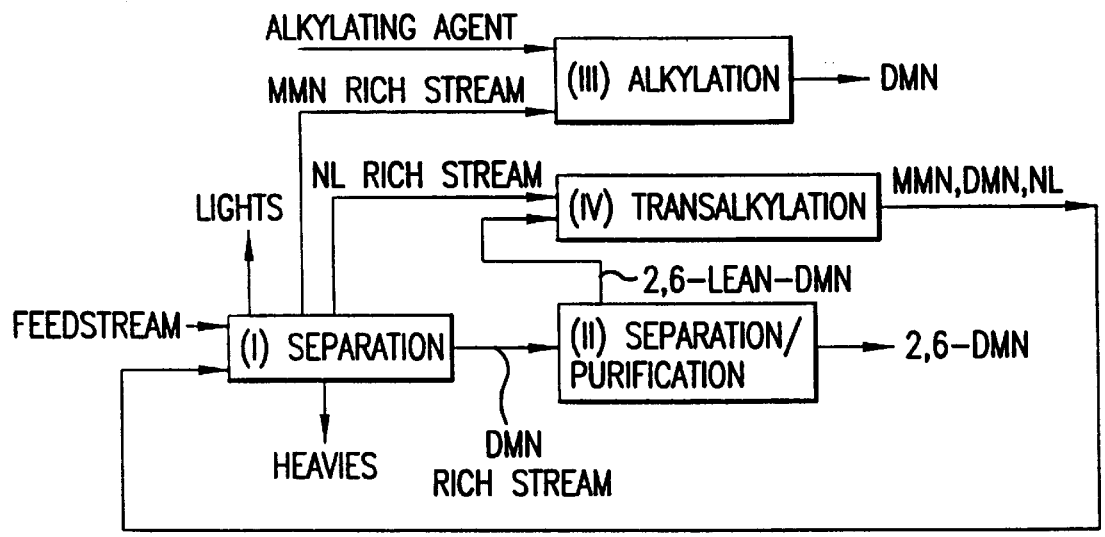
Figure 3D:
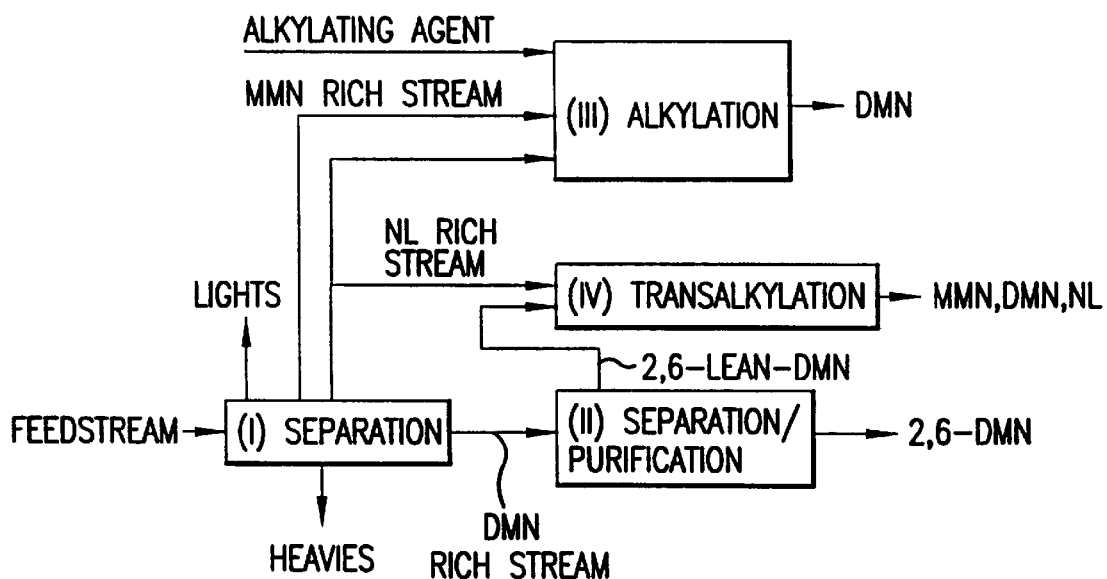
Figure 4A:
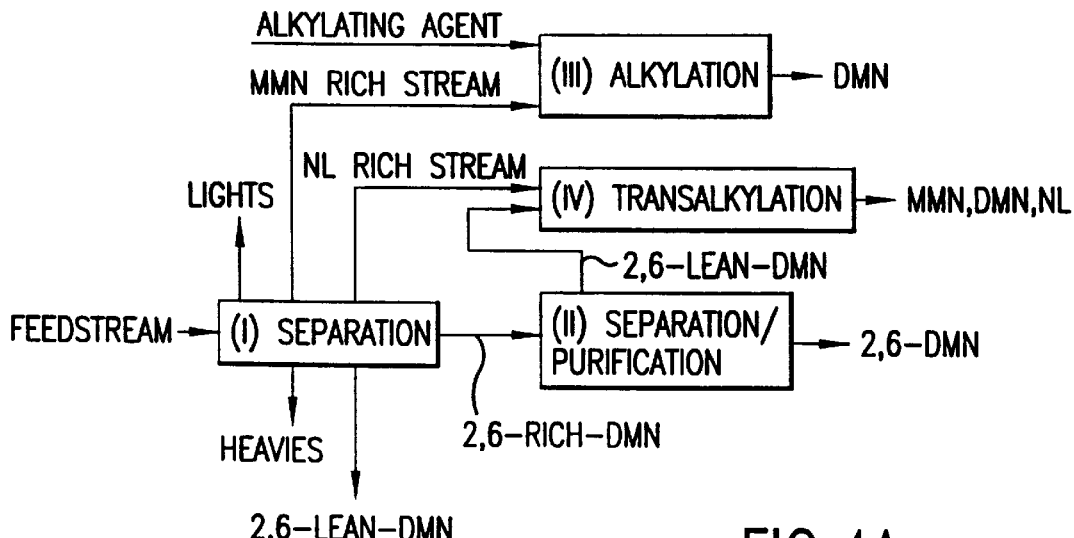
Figure 4B:
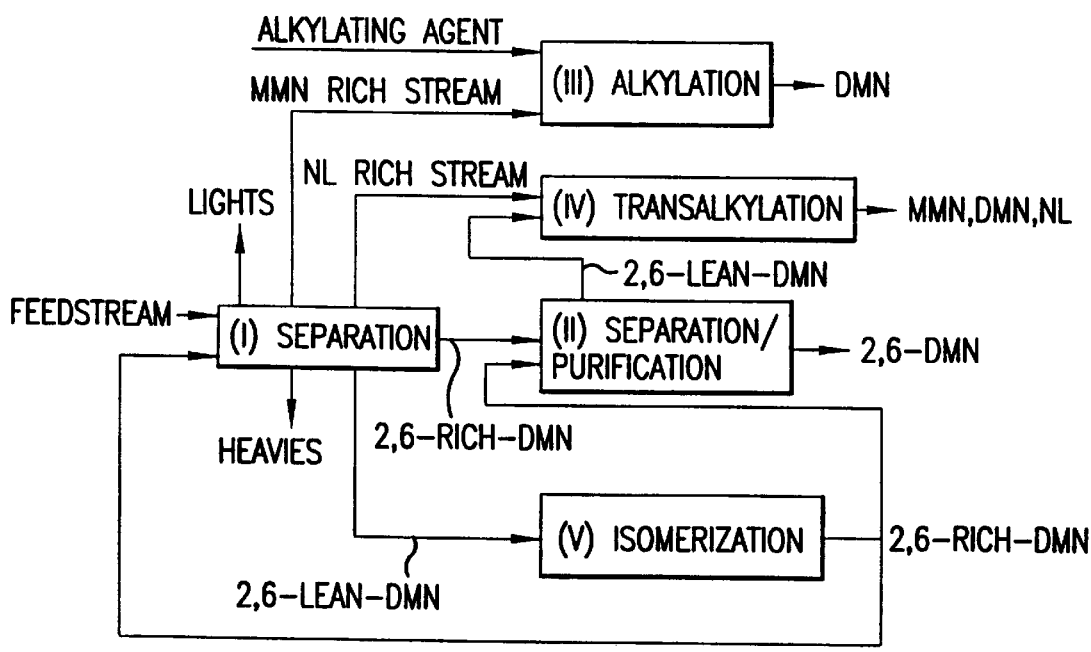
Figure 4C:
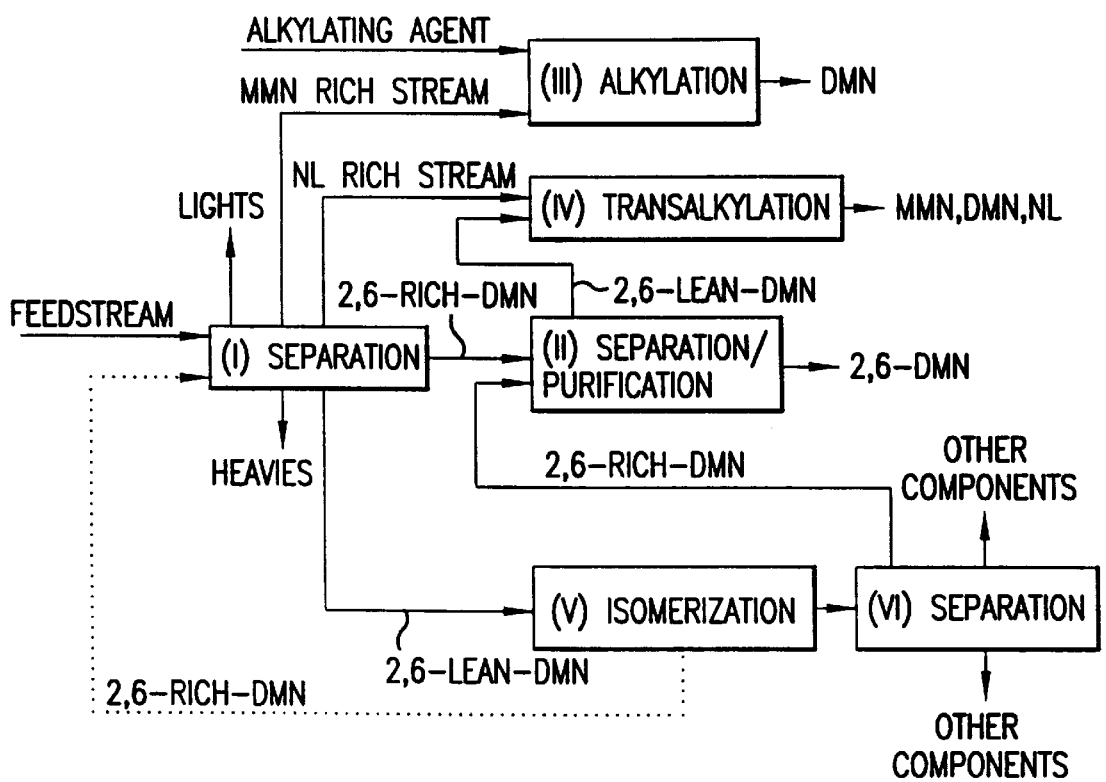
Figure 5A:
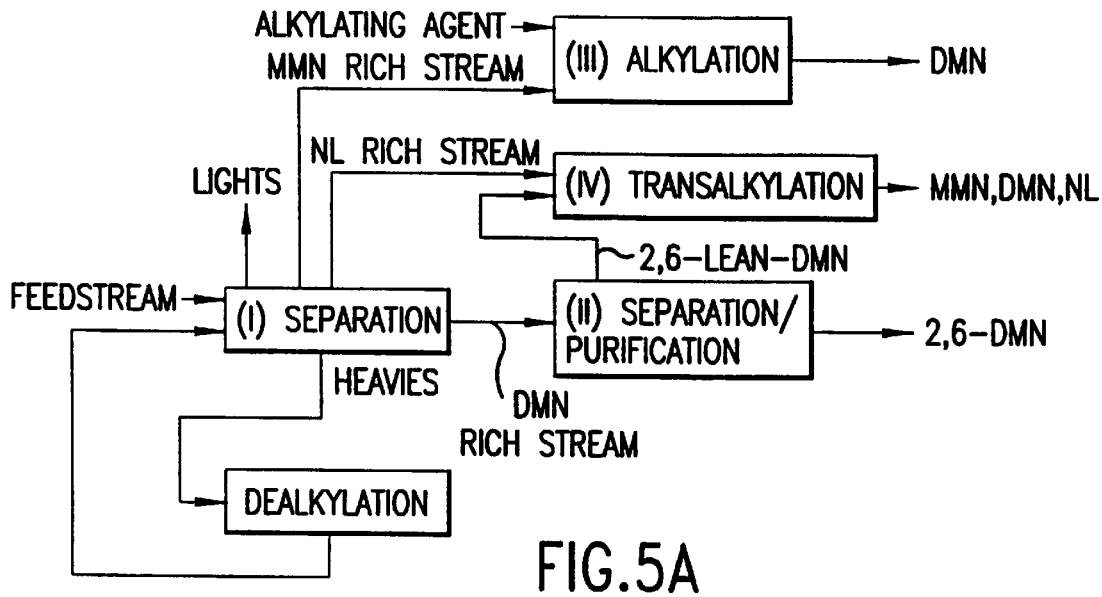
Figure 5B:
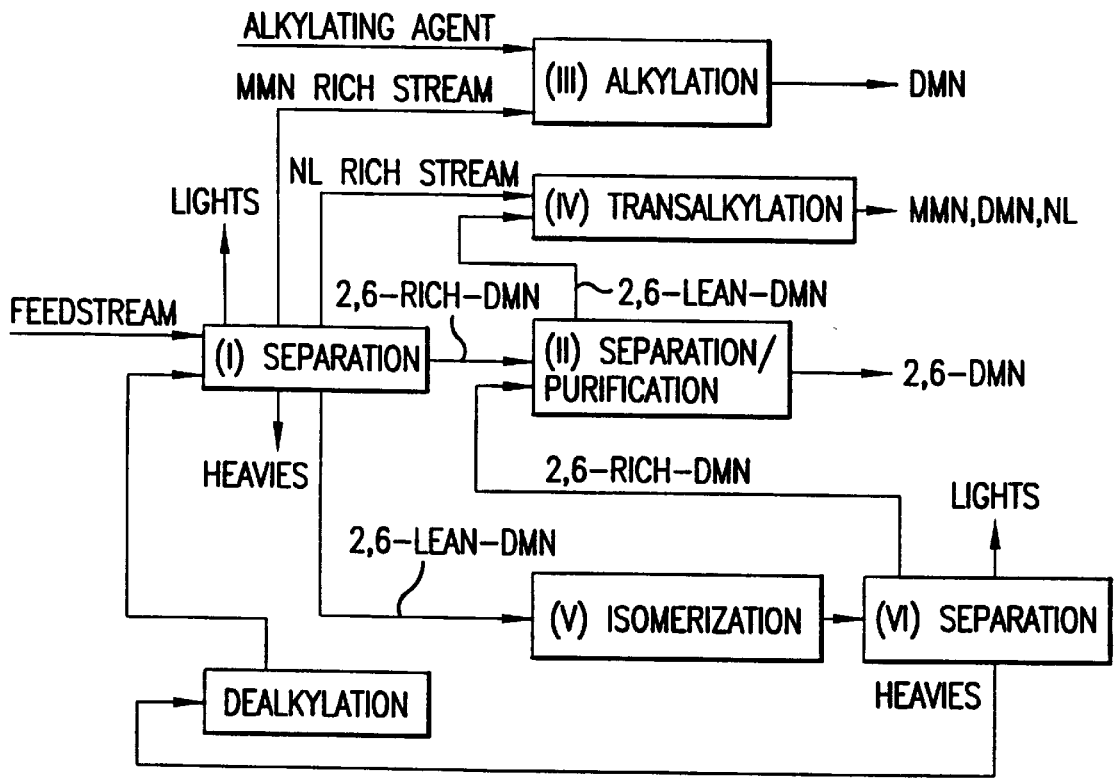
Figure 5C:
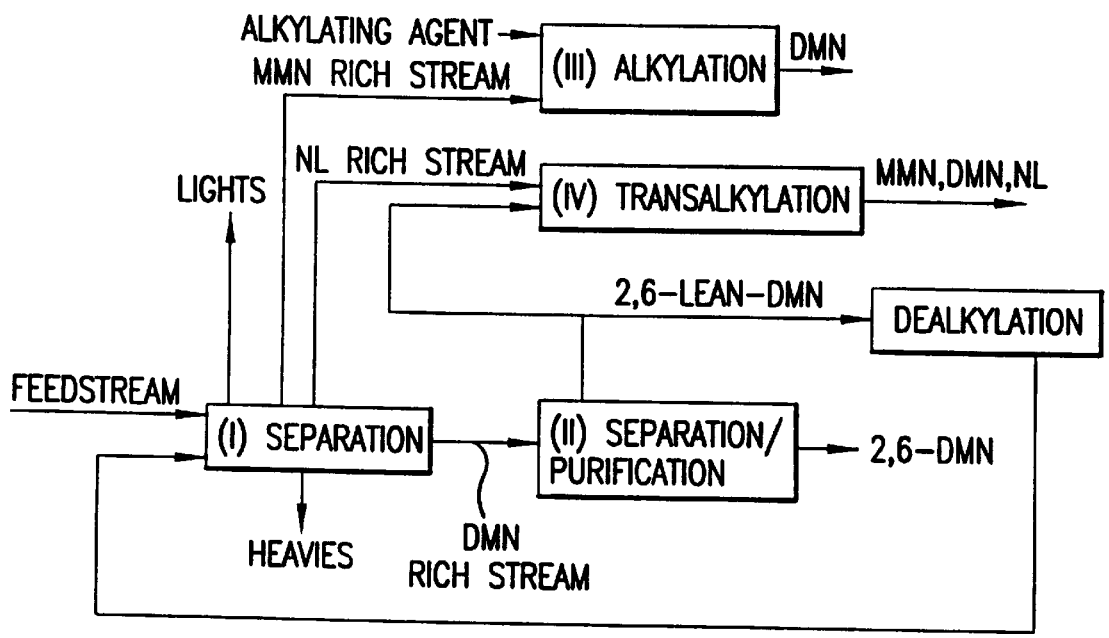
Figure 6A:
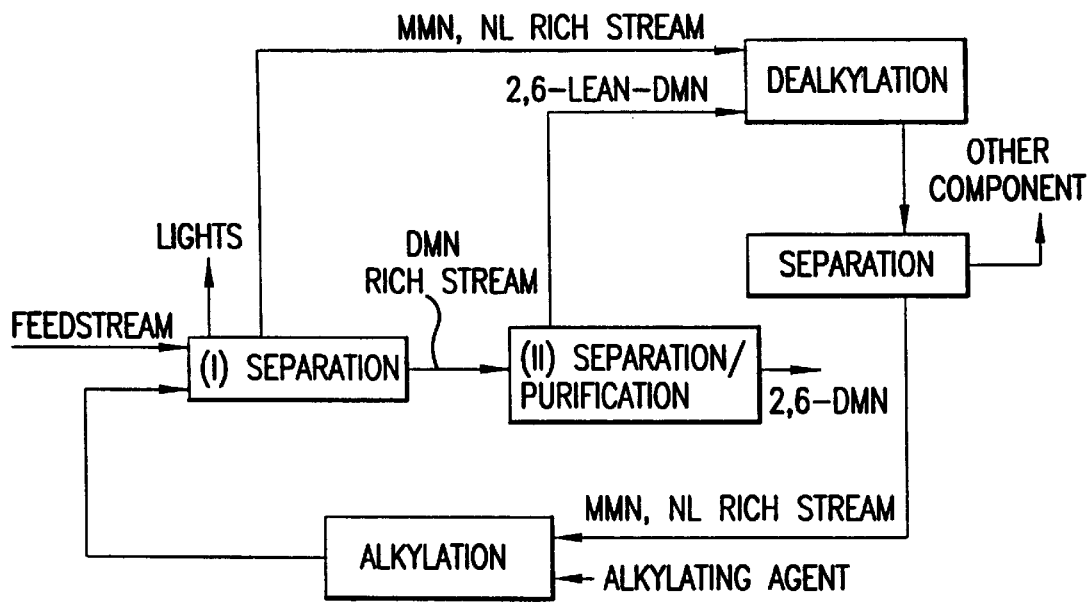
Figure 6B:
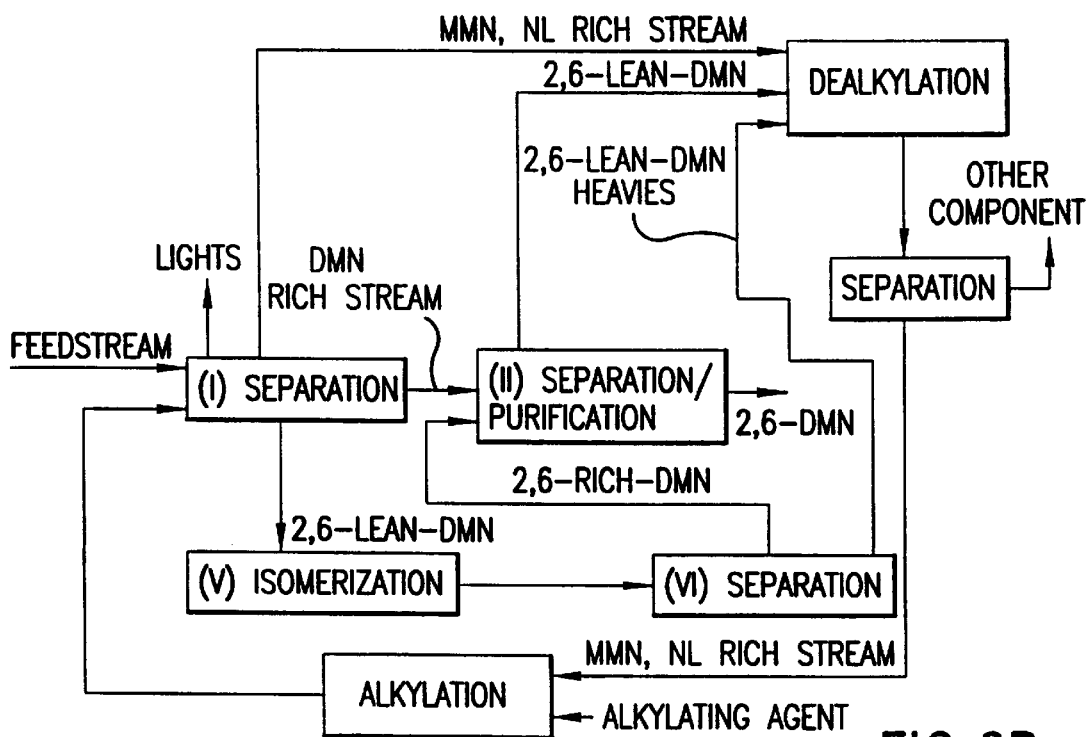
Figure 6C:
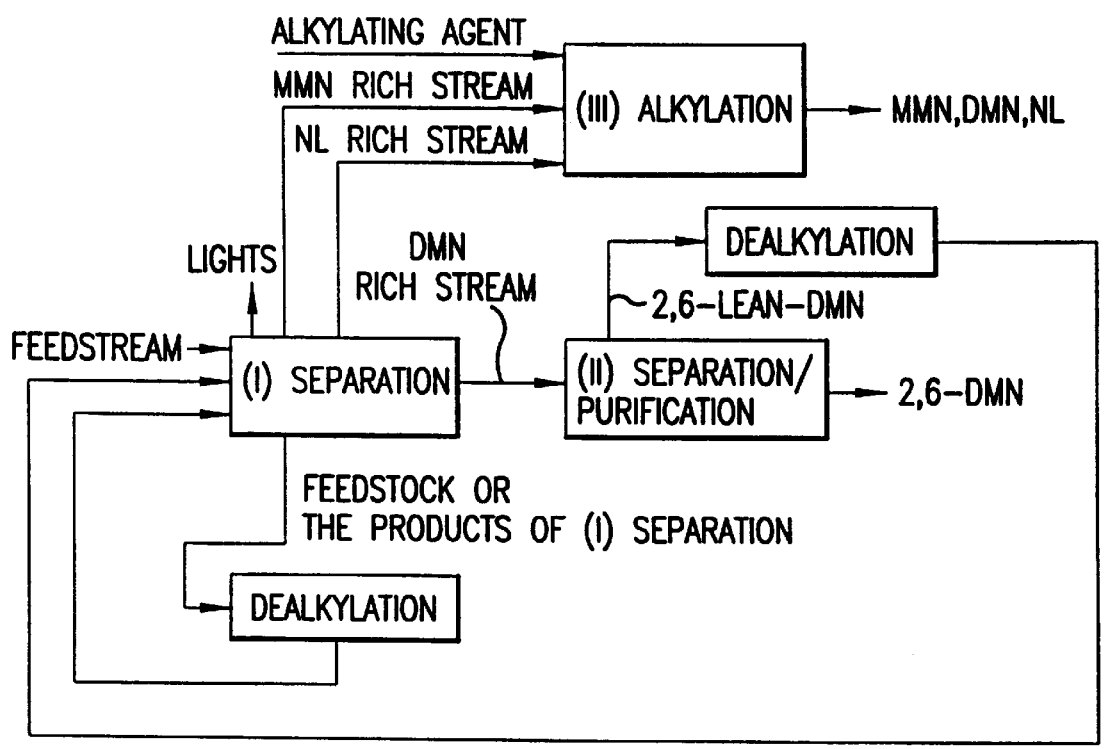
Figure 7A:
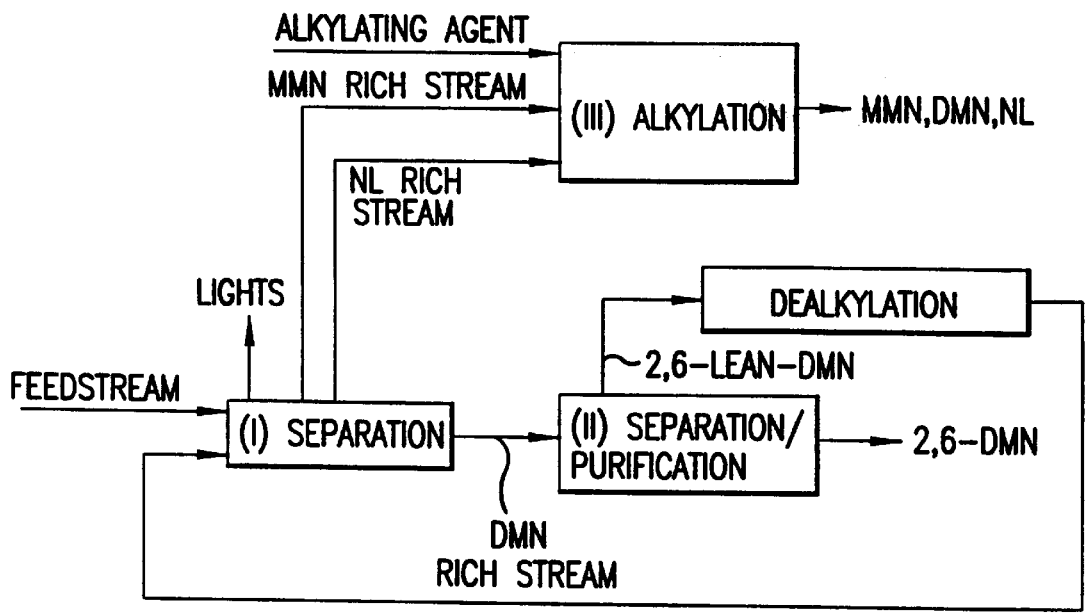
Figure 7B:
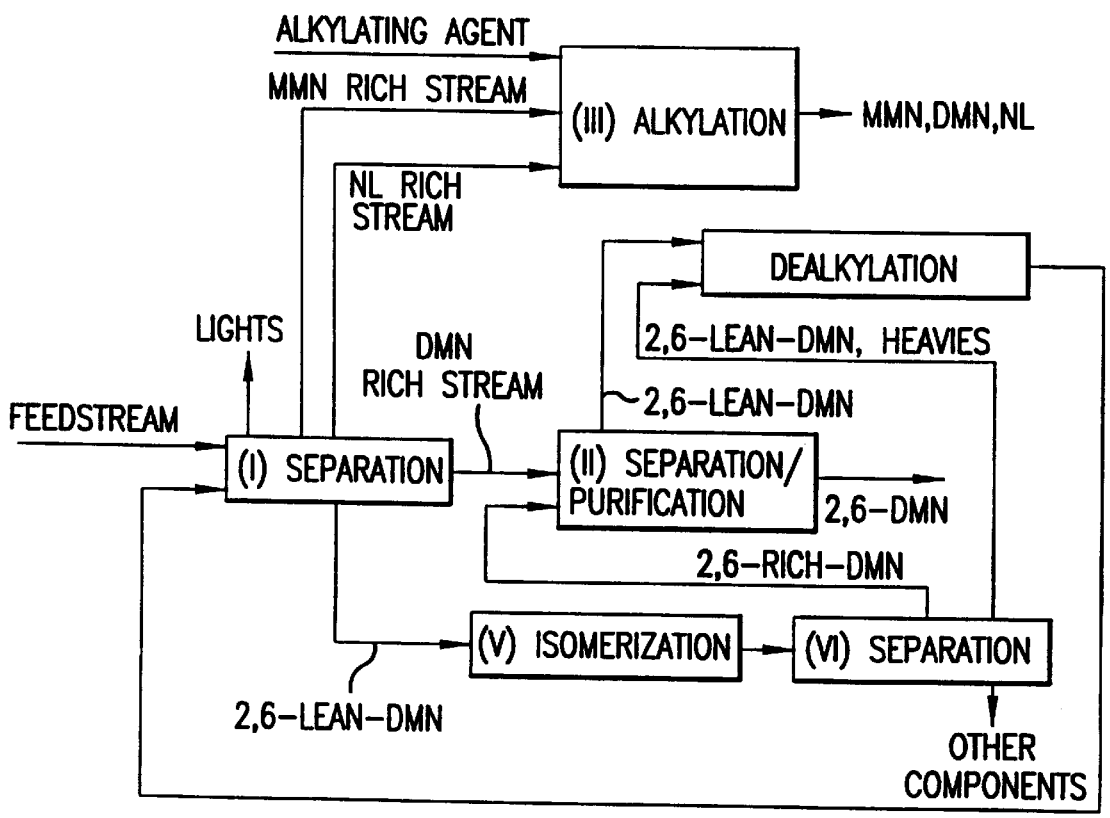
Figure 8:
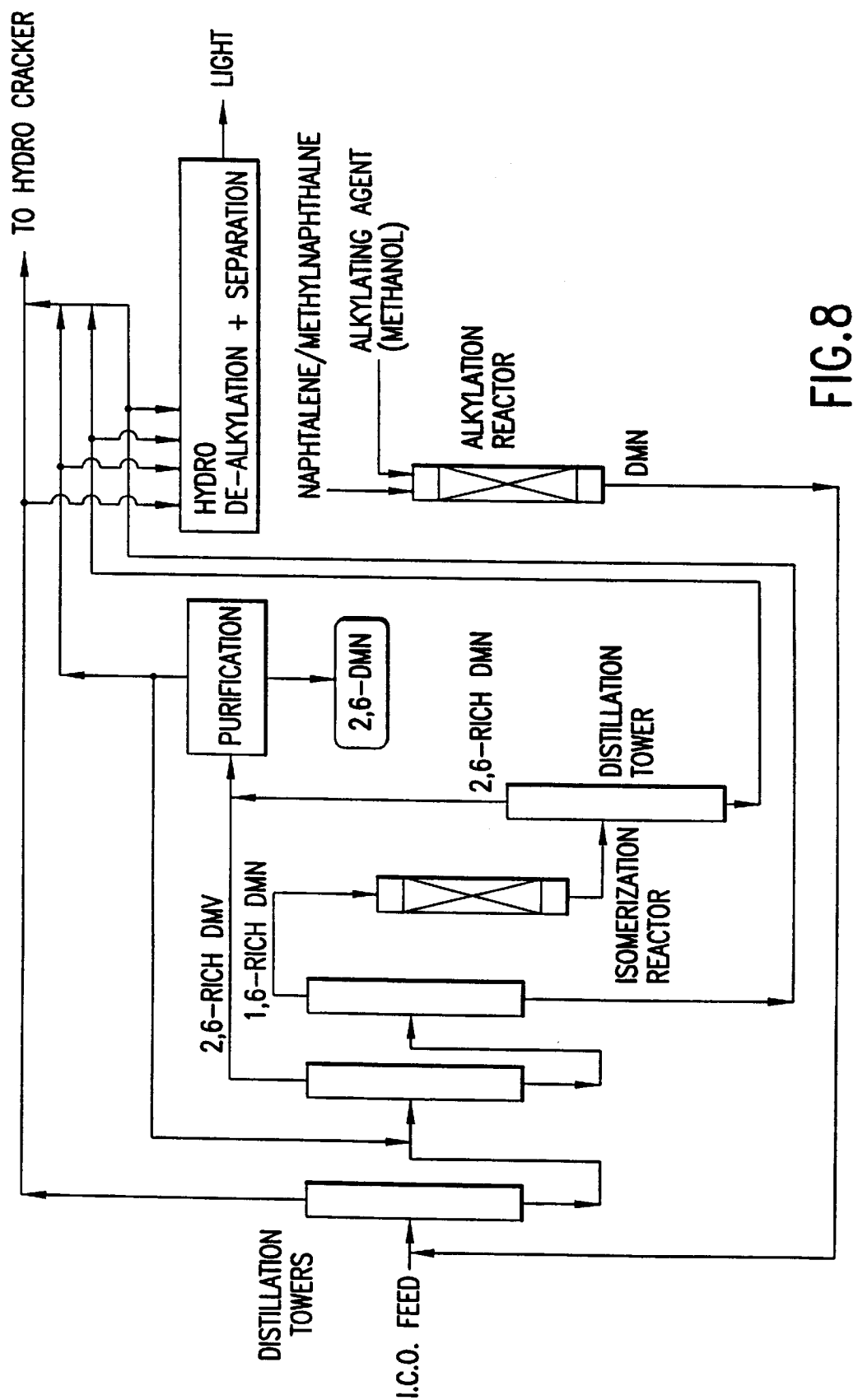

The present invention may be applied to any feed streams of hydrocarbons that contains alkylnaphthalenes, at least one of naphthalene, MMN (monomethylnaphthalene) and DMN isomers including 2,6-triad DMN (2,6-DMN and/or 1,6-DMN and/or 1,5-DMN). In particular, LCO (Light Cycle Oil) from FCC (Fluid Catalyst Cracking) or HC (Hydrocracker) is a preferable example of a feed stream.

As for the separation of LCO into each fraction of naphthalene, MMN and DMN conventional method such as distillation can be utilized. However, LCO usually contains many kinds of components such as light paraffins and mono-aromatics with long chain alkyl-group, which have similar boiling points to boiling points of naphthalene, MMN and DMN (Co-boilers). It is very hard to separate alkylnaphthalenes from their co-boilers only by distillation.

In such case, they can be separated from their co-boilers by conventional solvent extraction method in step (I). However, this present invention, including utilization of MCM-22 catalyst charged in reactors (alkylator, transalkylator and isomerizer) can reduce the load of extraction or eliminate it. If hydrogen is co-fed to the reactors, MCM-22 catalyst can effect a cracking reaction to convert co-boiler components into components having a higher vapor pressure than each of naphthalene, MMN and DMN.

Therefore, as the co-boilers can be reformed and changed to components having a higher vapor pressure at the outlet of alkylator, transalkylator and isomerizer and the product from the reactors are recycled to step (I) Distillation, it is possible to perform further separation and concentration of each of naphthalene, MMN and DMN in step (I) as the preferable feed stream of each reactor.

Alternatively co-boilers may be reformed by a combination with a conventional hydrodealkylation technique. In this case, the following advantages can be achieved;

i) Co-boilers contained in the feedstock can be easily changed and it makes easier to separate them by distillation from naphthalenes, monoalkylnaphthalenes and dialkylnaphthalenes.

ii) Paraffins and mono-aromatics with long chains can be reformed to usefull BTX (benzene, toluene, xylene) or a gasoline fraction.

iii) Alkylnaphthalenes including polyalkylnaphthalenes, which are contained in the feedstock and/or which are formed by reactions (alkylation and/or transalkylation and/or isomerization), can be reformed to pure naphthalenes and monoalkylnaphthalenes, which are preferable feedstock for the reaction.

iv) In case the feed stream contains sulfur and nitrogen compounds, which might be catalyst poisons, these compounds can be excluded from the recycling streams and products.

Refinery plants usually have FCC or HC for gasoline recovery from residues of atmospheric distillation unit. LCO is a by-product and its main use is as a diluent of A-heavy oil and/or C-heavy oil by being mixed with them. Therefore, LCO is evaluated as having fuel value. However, LCO usually contains naphthalene and alkylnaphthalenes such as MMN and DMN fraction at about 20 to 35 weight %. (alkylnaphthalenes/LCO).

The present invention provides an effective production process of 2,6-DMN as high-value added product by utilizing a non valuable feed stream.

As a feed stream for the present process, any hydrocarbon feedstream containing at least one of naphthalene, MMN or DMN, such as Light Cycle Oil (LCO) derived from Catalytically cracking petroleum oil may be used.

For the separation and concentration of step (I), conventional techniques such as distillation can be applied to step (I) may be used. In the case were the feed stream contains non-aromatic components which boiling points are very similar to naphthalene and/or MMN, conventional solvent extraction techniques also can be applied in addition to the above mentioned distillation in step (I).

The conditions of alkylation include a temperature of about 0 to 500 ° C., and preferably 240 and 450 ° C., and a pressure of between 0 to 250 atmospheres and preferably 1 to 50 atmospheres. The mole ratio of alkylating agent to feed of monalkylnaphthylene or naphthalene can be from about 20:1 to 1:20, preferably from 10:1 to 1:10. The reaction is suitably accomplished utilizing a feed space velocity of about 0.1 to 10.0 $hr^{-1}$.

Preferred alkylating agents include alcohols, olefins, aldehydes, halides, and ethers. For example, methanol, dimethylether and polyalkylbenzene are preferred. Methanol and dimethylether are especially preferred.

A suitable catalyst for alkylation, is a synthetic zeolite characterized by an X-ray diffraction pattern including interplanar d-spacing and relative intensity $I/I_o \times 100$

| | |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06Å | VS. |

A suitable catalyst is described in U.S. Pat. No. 5,001,295, as MCM-22.

The alkylation can be carried out in any of the known reactors usually employed for alkylation. For example, a tubular reactor with a downflow of reactants over a fixed bed of catalyst can be employed.

The conditions of transalkylation include a temperature of about 0 to 500° C., and preferably 200 to 450° C., and a pressure of 0 to 250 atmospheres and preferably 1 to 25 atmospheres. The mole ratio of naphthalene to DMN can be from about 10:1 to 10, preferably from 5:1 to 1:5. The reaction is suitably accomplished utilizing a feed space velocity of about 0.1 to 10.0 $hr^{-1}$.

A suitable catalyst for transalkylation, is a synthetic zeolite characterized by an X-ray diffraction pattern including interplanar d-spacing and relative intensity $I/I_o \times 100$

| | |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06Å | VS. |

A suitable catalyst is described in U.S. Pat. No. 5,001,295, as MCM-22.

Separation of 2,6-dialkylnaphthalene maybe conducted by conventional methods of separation known to those of ordinary skill in the art such as cooling crystallization or adsorption. For example separation may be affected by using a method of crystallization under high pressure. In general, a liquid mixture containing two or more substances is pressurized, and a certain substance in the mixture is solidified and separated from the residual liquid by the effect of the pressure. In other words, this method involves a separating and purifying technique wherein a liquid mixture containing two or more substances is placed in a tightly sealed pressure vessel, a portion of the desired substance, 2,6-dialkylnaphthalene, is solidified to form a solid-liquid co-existing state, the liquid is discharged from the co-existing system while maintaining the pressure of the solid-liquid co-existing system at a higher level than equilibrium pressure of the objective substance, then the solid remaining in the vessel is pressed for discharging the residual liquid between the solid particles and integrating the solid particles. This technique is generally described in U.S. Pat. No. 5,220,098.

The method involves injecting the slurry or liquid of the temperature of 70 to 120° C., preferably 80 to 100° C., into a high pressure vessel for conducting a crystallization under high pressure; adiabatically pressurizing the vessel to a pressure of from 300 to 4,000 kgf/cm², preferably 500 to 2,000 kgf/cm² to increase the quantity, i.e. the amount of 2,6-dialkylnaphthalene crystals, whereby coexistence of solid-liquid phases exist at the high pressure conditions; discharging the liquid phase component from the high pressure vessel, the discharging being conducted under pressure, to increase the ratio of the solid phase relative to the liquid phase within the vessel; lowering the pressure of the residual liquid phase so as to dissolve partially and purify the product; discharging the residual liquid phase by applying pressure to the solid phase within the high pressure vessel whereby a 2,6-dialkylnaphthalene crystal block having a high purity is obtained within the high pressure vessel. By this technique, a purity of 2,6 dialkylnaphthalene (e.g. 2,6-dimethylnaphthylene) of ≧98% by weight, preferably ≧99% by weight may be obtained.

In a preferred embodiment, a 2,6-lean dialkylnaphthalene fraction may be subject to isomerization conditions to provide for a dialkylnaphthalene fraction which has a greater content of 2,6-dialkylnaphthalene.

Isomerization conditions are those generally as disclosed in co-pending application U.S. Pat. No. 08/661,114, as suitable for conducting simultaneous transalkylation of dialkylnaphthalene and naphthalene, and isomerization of dialkylnaphthalenes, the relevant portions of which are hereby incorporated by reference.

As a suitable catalyst for isomerisation, a synthetic zeolite characterized by an X-ray diffraction pattern including interplanar d-spacing and relative intensity $I/I_o 100$

| | |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06Å | VS. |

A suitable catalyst is described in U.S. Pat. No. 5,001,295, as MCM-22, the entire contents of which are hereby incorporated by reference.

Preferably, isomerization is conducted at a weight hourly space velocity (WHSV) of dialkylnaphthalenes of 0.1 to 10, preferably 0.5 to 5 $h^{-1}$, more preferably 0.75 to 1.5 $h^{-1}$.

Preferably, isomerization is conducted at a temperature of from 100 to 500° C., preferably 150 to 350° C., more preferably 200 to 300° C.

Preferably, isomerization is conducted at a pressure of atmospheric to 100 kgf/cm², preferably atmospheric to 30 kgf/cm².

During isomerization it is possible to co-feed of hydrogen, but is not always necessary, in an amount of 0.1 to 10 mol-$H_2$/mol-hydrocarbons.

The resulting 2,6-dialkylnaphthalene, e.g. 2,6-dimethylnaphthalene may then be used to produce a polyester resin, by oxidation of 2,6-dimethylnaphthalene to form 2,6-naphthalenedicarboxylic acid, by conventional methods known to those of ordinary skill in the art.

The 2,6-naphthalenedicarboxylic acid may then be condensed with a diol such as ethylene glycol, propylene glycol, butane diol, pentane diol and hexane diol. In a preferred embodiment, the polyester resin formed in a polyethylenenaphthalate or polybutylenenaphthalate resin. Such a condensation may be conducted by conventional methods known to those of ordinary skill in the art.

Alternatively a polyester resin may be formed from 2,6-naphthalenedicarboxylic acid by first esterification of 2,6-naphthalenedicarboxylic acid with an alcohol such as a $C_{1-6}$ alcohol, such as methanol, ethanol, propanol, isopropanol, n-butanol, s-butanol, i-butanol, t-butanol. In a preferred embodiment, the alcohol is methanol. Esterification may be conducted by conventional techniques known to those of ordinary skill in the art. The alkylester of 2,6-naphthalenedicarboxylic acid by then be condensed with a diol as described above, by conventional methods known to those of ordinary skill in the art. Suitable diols include ethylene glycol, propylene glycol, butane diol, pentane diol and hexane diol. In a preferred embodiment the diol is either ethylene glycol or butane diol.

Having generally described this invention, a further understanding can be obtained by reference to certain specific examples which are provided herein for purposes of illustration only and are not intended to be limiting unless otherwise specified.

EXAMPLES

Example 1 Alkylation of MMN and Naphthalene:

A 153 g amount of MCM-22 is charged into a tubular reactor (volume:370 cc). As a feedstock for alkylation, 1-MMN, 2-MMN and naphthalene are used, and mixed at a molar ratio of 2.2 of 2-MMN/1-MMN, and a weight ratio of 3.0 of MMNs (1-MMN+2-MMN)/naphthalene.

Thereupon, the feedstock is supplied to the reactor (254° C., 5 kg/cm²) at a rate of 153.4 g/hr and 1.0 $hr^{-1}$ in WHSV with a feed of hydrogen at the rate of 1.8 ft³/hr. Four hours later, methanol, as an alkylating agent, is introduced into the reactor at 35.5 g/hr, and alkylation is conducted for 20 hours. The product obtained is analyzed by gas chromatography, and the results are summarized in Table 1.

TABLE 1

Alkylation of Monomethylnaphthalene and Naphthalene

| | before reaction | after reaction |
|---|---|---|
| Component (wt %) | | |
| dimethylnaphthalene | 0 | 17.19 |
| 2,6-DMN | 0 | 1.72 |
| 2,7-DMN | 0 | 1.20 |
| other isomers | 0 | 14.27 |
| monomethylnaphthalene | 73.63 | 60.10 |
| 2-MMN | 50.55 | 40.32 |
| 1-MMN | 23.08 | 19.78 |

TABLE 1-continued

Alkylation of Monomethylnaphthalene and Naphthalene

|  | before reaction | after reaction |
|---|---|---|
| naphthalene | 25.28 | 18.67 |
| other component | 1.00 | 3.91 |
| evaluation |  |  |
| NL conversion (%) | — | 26.15 |
| 2-MMN/1-MMN | 2.2 | 2.04 |
| MMN conversion (%) | — | 18.37 |
| 2,6-DMN/total DMN (%) | — | 10.02 |
| 2,6-DMN/2,7-DMN | — | 1.44 |

As can be seen from Table 1, the ratio of 2,6-DMN/2,7-DMN is over 1.1 and the ratio of 2-MMN/1-MMN is over 2.0.

Example 2 Transalkylation:

A 30 g amount of MCM-22 (1/16" D×3/8"L, cylindrical pellet) are charged into a tubular reactor (volume: 122 cc). The reactor is heated from room temperature to 400° C. at the rate of 100° C./hr while introducing nitrogen gas into the reactor at atmospheric pressure.

As a feedstock for transalkylation, isomers of DMN and naphthalene are mixed in a molar ratio of 5:1. Feedstock and product analysis are shown in Table 2.

TABLE 2

Transalkylation and Isomerization

|  | before reaction | after reaction |
|---|---|---|
| Component (wt %) |  |  |
| dimethylnaphthalene | 84.37 | 65.91 |
| 2,6-DMN | 5.22 | 11.39 |
| 2,7-DMN | 7.28 | 7.42 |
| other isomers | 71.87 | 47.10 |
| monomethylnaphthalene | 0.17 | 13.81 |
| 2-MMN | 0.02 | 9.54 |
| 1-MMN | 0.15 | 4.27 |
| naphthalene | 15.46 | 12.65 |
| other component | 0 | 7.63 |
| evaluation |  |  |
| 2,6-DMN/total DMN (%) | 6.2① | 17.3② |
| 2,6-DMN/2,7-DMN | 0.72 | 1.53 |
| content of 2,6-DMN (after/before): @1 | — | 2.79 |
| NL conversion (%) | — | 18.2 |
| DMN conversion (%) | — | 21.9 |
| produced MMN/(converted DMN × 2): @2 | — | 0.41 |
| 2-MMN/1-MMN | — | 2.2 |

@1 The ratio of ②/① in 2,6-DMN/total DMN
@2 Amounts are calculated on a molar basis.

As can be seen from Table 2, the ratio of 2,6-DMN/2,7-DMN is over 1.2 and the ratio of 2-MMN/1-MMN is over 2.0.

Example 3 Isomerization:

A 25 g amount of MCM-22 is charged into the tubular reactor (volume: 200 cc). The reactor is heated gradually from ambient temperature to 400° C. to dry the catalyst while supplying nitrogen gas, and the flow of nitrogen gas is ceased when the temperature becomes stable at 400° C. Thereupon, 2,6-lean-DMN is supplied to the reactor at the rate of 25 g/hr and 1.0 hr$^{-1}$ in WHSV, and isomerization of DMN is carried out for four hours. The contents of the obtained product are analyzed by gas chromatography, and the results are summarized in Table 3.

TABLE 3

Isomerization

|  | before reaction | after reaction |
|---|---|---|
| Component (wt %) |  |  |
| dimethylnaphthalene | 98.09 | 80.10 |
| 2,6-DMN | 6.21 | 13.96 |
| 2,7-DMN | 8.48 | 8.66 |
| other isomers | 83.40 | 57.48 |
| monomethylnaphthalene | 0.20 | 9.77 |
| 2-MMN | 0.03 | 6.71 |
| 1-MMN | 0.17 | 3.06 |
| naphthalene | 0 | 0.78 |
| other component | 1.71 | 9.35 |
| evaluation |  |  |
| 2,6-DMN/total DMN (%) | 6.3 | 17.4 |
| 2,6-DMN/2,7DMN | 0.73 | 1.61 |

As can be seen from Table 3, the ratio of 2,6-DMN/2,7-DMN is over 1.1.

Example 4 Separation of Purification:

(1) Crystallization under High Pressure Crystallization

A 1,505 g amount of DMN isomers is supplied into the high pressure crystallizer (KOBELCO 1.5 L type), and 236 g of 2,6-DNN crystals (purity 87%) are separated under the condition of 2,000 kgf/cm$^2$ and 45° C.

(2) Cooling Crystallization

Using a vessel for crystallization (3 liter), 2,001 g of DMN isomers is cooled quickly from 50° C. to 40° C. with slow stirring. Then, 0.5 g of seed crystals are charged to the vessel which is kept at a temperature at 40° C. for an hour. Thereupon, the feedstock is cooled to 10° C. at 2° C./min. A 360 g amount of 2,6-DMN crystals (purity 68%) is separated by filtration under pressure.

The results of separation by both crystallization under high pressure and cooling crystallization are summarized in Table 4.

TABLE 4

Separation

| Component (g) | before crystallization | crystal | filtrate |
|---|---|---|---|
| CRYSTALLIZATION UNDER HIGH PRESSURE ||||
| 2,6-DMN | 301 | 205 | 96 |
| 2,7-DMN | 232 | 22 | 210 |
| other DMN | 972 | 9 | 963 |
| TOTAL | 1505 | 236 | 1269 |
| 2,6-DMN/2,7-DMN | 1.3 | — | 0.5 |
| 2,6-DMN/total DMN | 20.0% | — | 7.6% |
| purity of crystal | — | 87% | — |
| recovery of 2,6-DMN | — | 68% | — |
| yield of 2,6-DMN | — | 13.6% | — |
| COOLING CRYSTALLIZATION ||||
| 2,6-DMN | 400 | 244 | 156 |
| 2,7-DMN | 308 | 67 | 241 |
| other DMN | 1293 | 49 | 1244 |
| TOTAL | 2001 | 360 | 1641 |
| 2,6-DMN/2,7-DMN | 1.3 | — | 0.65 |
| 2,6-DMN/total DMN | 20.0% | — | 9.5% |

TABLE 4-continued

| Component (g) | Separation | | |
|---|---|---|---|
| | before crystallization | crystal | filtrate |
| purity of crystal | — | 68% | — |
| recovery of 2,6-DMN | — | 61% | — |
| yield of 2,6-DMN | — | 12.2% | — |

"Recovery of 2,6-DMN" means the content of 2,6-DMN in the crystals against the content of 2,6-DMN in the feedstock.

"Yield of 2,6-DMN" means the content of 2,6-DMN in the crystal against the total weight of feedstock.

As shown in Table 4, the yield of 2,6-DMN by crystallization under high pressure is much higher than by cooling crystallization. Further, the 2,6-DMN/total-DMN ratio of the filtrate by crystallization under high pressure is less than 8%. Therefore, the filtrate is more effective as a feedstock for transalkylation and isomerization of 2,6-lean-DMN. Furthermore, when an attempt is made to increase the purity of crystals by cooling crystallization, the yield of 2,6-DMN decreases drastically.

Example 5 Cracking of Distillates from LCO

Example of Cracking

A 50 g amount of MCM-22 is charged into a tubular reactor. The reactor is heated gradually from ambient temperature to 325° C. to dry the catalyst while supplying hydrogen gas. Thereupon LCO distillate (Table 5) is supplied to the reactor at the rate of 50 g/hr and 1.0 hr$^{-1}$ in WHSV, while supplying hydrogen gas at 10 1/hr. The reaction was conducted at 325, 355, 375, and 405° C. The results of cracking are sunmarized in Table 6 below. Initial boiling point data shows that cracking was conducted by contacting LCO feedstock with MCM-22.

Feed stock:

Heart Cut Distillate from Batch Distillation of LCO

Number of Trays=18

Press=20 Torr

Reflux Ratio=10

Initial Boiling Point: 167° C. (by ASTM D-2887)

Components

TABLE 5

| | wt. % |
|---|---|
| Naphthalene | 4.02 |
| 2-Methylnaphthalene | 12.56 |
| 1-Methylnaphthalene | 6.00 |
| 2,6-DMN | 0.58 |
| 2,7-DMN | 0.54 |
| 1,3- + 1,7-DMN | 0.8 |
| 1,6-DMN | 0.34 |
| 2,3- + 1,4-DMN | 0.12 |
| 1,5-DMN | 0.07 |
| 1,2-DMN | 0.06 |
| 1,8-DMN | 0 |
| Others | 74.91 |

Cracking Conditions:

Catalyst: MCM-22(50 gm in Tubular Reactor)

Press.: 15 kg/cm$^2$

Rate: 50 gm/hr

Hydrogen in Reactor: 10 lit/hr

Temp.: 325° C., 355° C., 275° C., 405° C.

Results:

TABLE 6

| Reaction Temp.[° C.] | Initial Boiling Point [° C.] ASTM D-2887 |
|---|---|
| Feed | 167 |
| 325 | 129 |
| 355 | 104 |
| 375 | 61 |
| 405 | 29 |

Obviously, numerous modifications and variations of the present invention are possible in light of the above teachings. It is therefore to be understood that within the scope of the appended claim, the invention may be practiced otherwise than as specifically described herein.

What is claimed as new and is desired to be secured by Letters Patent of the United States is:

1. A process for producing 2,6-dialkylnaphthalene from a feedstock, comprising the following steps:
   I. separating said feedstock into a naphthalene, monoalkynaphthalene, dialkylnaphthalene fractions:
   II. separating and purifying 2,6-dialkylnaphthalene from said dialkylnaphthlane fraction of step I to produce 2,6-dialkylnaphthalene and a second dialkylnaphthalene fraction;
   III. alkylating said monoalkylnaphthalene fraction of step I with an alkylating agent to produce dialkylnaphthalene and recycling the dialkylnaphthalene to step I;
   IV. transalkylating said naphthalene fraction of step I and said second dialkylnaphthalene fraction produced in step II, to produce monoalkylnaphthalene, and isomers of dialkylnaphthalene; wherein said monoalkynaphthalene fraction produced in step I is cracked before step III, or in step III, or after step III.

2. The process of claim 1, wherein at least one of said monoalkylnaphthalene, and isomers of dialkylnaphthalene produced in step IV is recycled to step I.

3. The process of claim 2, further comprising cracking of said dialkylnaphthalene fraction and said naphthalene fractions before step IV, or in step IV, or after step IV.

4. The process of claim 1, wherein at least a portion of said naphthalene fraction in step I is fed to step III to be alkylated with said alkylating agent.

5. The process of claim 1, wherein at least step III or step IV is conducted in the presence of a catalyst composition comprising a synthetic zeolite.

6. The process of claim 5, wherein the catalyst having a composition comprising a synthetic zeolite is characterized by an X-ray diffraction pattern including interplanar d-spacing (A)

12.36±0.4

11.03±0.2

8.83±0.14

6.18±0.12

6.00±0.10

4.06±0.07

3.91±0.07

3.42±0.06.

7. The process of claim 1, further comprising (i) separating said dialkylnaphthalene fraction from step I into 2,6-rich-dialkylnaphthalene and 2,6-lean-dialkylnaphthalene fractions, wherein said 2,6-rich-dialkylnaphthalene fraction is utilized in separating and purifying 2,6-dialkylnaphthalene in step II.

8. The process of claim 7, further comprising isomerizing said 2,6-lean-dialkylnaphthalene fraction in the presence of a catalyst, wherein the product in said isomerization is fed to step II and/or step I.

9. The process of claim 8, further comprising cracking of co-boiler of dialkynaphthalene at said 2,6-lean-dialkylnaphthalene stream before isomerization, or with the isomerization, or after isomerization and before step I.

10. The process of claim 8, wherein at least a part of the product in said isomerization is separated into a 2,6-rich-dialkylnaphthalene fraction and other components, and said 2,6-rich-dialkylnaphthalene fraction is fed to step II.

11. The process of claim 8, wherein the isomerization is conducted in the presence of a catalyst composition comprising a synthetic zeolite.

12. The process of claim 8, wherein the catalyst having a composition comprising a synthetic zeolite is characterized by an X-ray diffraction pattern including interplanar d-spacing (A)

12.36±0.4
11.03±0.2
8.83±0.14
6.18±0.12
6.00±0.10
4.06±0.07
3.91±0.07
3.42±0.06.

13. The process of claim 1, wherein at least a part of the feedstock or at least a part of said monoalkylnaphthalene fraction produced in step I is dealkylated, then recycled to step I.

14. The process of claim 7, wherein at least a part of the other components containing alkylnaphthalene having a higher boiling point than naphthalenes in the separation after the isomerization are dealkylated, then recycled to step I.

15. The process of claim 1, wherein a part of said dialkynaphthalene fraction after 2,6-dialkylnaphthalene is separated therefrom in step II are dealkylated, then recycled to step I.

16. The process of claim 1, wherein separation in step I is conducted by distillation, or distillation and extraction.

17. The process of claim 1, wherein 2,6-dialkylnaphthalene is separated by crystallization under high pressure in step II.

18. The process of claim 1, wherein said dialkylnaphthalene is dimethylnaphthalene and said monoalkylnaphthalene is monomethylnaphthalene.

19. The process of claim 1, wherein said alkylating agent is methanol or dimethylether.

20. A process of preparing a polyethylenenaphthalate polymer or polybutylenenaphthalate polymer comprising;
   A. oxidizing 2,6-dialkylnaphthalene to form 2,6-naphthalene-dicarboxylic acid; and
   B. condensing said 2,6-naphthalene-dicarboxylic acid with a diol selected from the group consisting of ethylene glycol and butanediol to form a polyethylenenaphthalate polymer or polybutyrenenaphthalete polymer
   wherein said 2,6-dialkylnaphthalene is produced by a process comprising the following steps:
   I. separating a feedstock into a naphthalene, monoalkynaphthalene, dialkylnaphthalene fractions:
   II. separating and purifying 2,6-dialkylnaphthalene from said dialkylnaphthlane fraction of step I to produce 2,6-dialkylnaphthalene and a second dialkylnaphthalene fraction;
   III. alkylating said monoalkylnaphthalene fraction of step I with an alkylating agent to produce dialkylnaphthalene;
   IV. transalkylating said naphthalene fraction of step I and said second dialkylnaphthalene fraction produced in step II, to produce monoalkylnaphthalene, and isomers of dialkylnaphthalene; wherein
   said monoalkynaphthalene fraction produced in step I is cracked before step III, or in step III, or after step III.

21. A process for preparing a polyethylene naphthalate polymer or polybutyrenenaphthalate polymer comprising;
   A. oxidizing 2,6-dialkylnaphthalene to form 2,6-naphthalene-dicarboxylic acid; and
   B. esterifying 2,6-naphthalene-dicarboxylic acid with methanol to form dimethyl-2,6-naphthalene-dicarboxylate; and
   C. condensing said dimethyl-2,6-naphthalene-dicarboxylate with diol selected from the group consisting of ethylene glycol and butanediol to form a polyethylenenaphthalate polymer or polybutyrenenaphthalate polymer
   wherein said 2,6-dialkylnaphthalene is produced by a process comprising the following steps:
   I. separating a feedstock into a naphthalene, monoalkynaphthalene, dialkylnaphthalene fractions:
   II. separating and purifying 2,6-dialkylnaphthalene from said dialkylnaphthlane fraction of step I to produce 2,6-dialkylnaphthalene and a second dialkynaphthalene fraction;
   III. alkylating said monoalkylnaphthalene fraction of step I with an alkylating agent to produce dialkylnaphthalene;
   IV. transalkylating said naphthalene fraction of step I and said second dialkylnaphthalene fraction produced in step II, to produce monoalkylnaphthalene, and isomers of dialkylnaphthalene; wherein
   said monoalkynaphthalene fraction produced in step I is cracked before step III, or in step III, or after step III.

22. A process for producing 2,6-dialkylnaphthalene from a feedstock, comprising the following steps:
   I. separating said feedstock into a fraction comprising naphthalene and monoalkynaphthalene and a fraction comprising dialkylnaphthalene;
   II. separating and purifying 2,6-dialkylnaphthalene from said dialkylnaphthalene fraction of step I to produce 2,6-dialkylnaphthalene and a second dialkynaphthalene fraction;
   III. dealkylating said naphthalene and monoalkynaphthalene fraction of step I and said second dialkylnaphthalene fraction produced in step II;
   IV. separating a naphthalene and monoalkynaphthalene fraction from said dealkylation product of step III;
   V. alkylating said naphthalene and monoalkynaphthalene fraction of step IV; and
   VI. recycling a product from step V to step I.

23. A process for producing 2,6-dialkylnaphthalene from a feedstock, comprising the following steps:
   I. separating said feedstock into a fraction comprising naphthalene and monoalkynaphthalene, a fraction comprising dialkylnaphthalene and a fraction lean in dialkylnaphthalene;
   II. separating and purifying 2,6-dialkylnaphthalene from said dialkylnaphthalene fraction of step I to produce 2,6-dialkylnaphthalene and a second dialkylnaphthalene fraction;

IIa. isomerizing said fraction lean in dialkylnaphthalene;

IIb. separating the isomerization product of step IIa into a fraction comprising dialkylnaphthalene and a fraction lean in dialkylnaphthalene;

IIc. feeding said fraction comprising dialkylnaphthalene of step IIb to step II;

III. dealkylating said naphthalene and monoalkynaphthalene fraction of step I, said second dialkylnaphthalene fraction produced in step II and a fraction lean in dialkylnaphthalene from step IIb;

IV. separating a naphthalene and monoalkynaphthalene fraction from said dealkylation of step III;

V. alkylating said naphthalene and monoalkynaphthalene fraction of step IV; and

VI. recycling a product from step V to step I.

24. A process for producing 2,6-dialkylnaphthalene from a feedstock, comprising the following steps:

I. separating said feedstock into a fraction comprising naphthalene, a fraction comprising monoalkynaphthalene, a fraction comprising dialkylnaphthalene and a fraction comprising remaining products;

II. separating and purifying 2,6-dialkylnaphthalene from said dialkylnaphthalene fraction of step I to produce 2,6-dialkylnaphthalene and a second dialkylnaphthalene fraction;

IIa. dealkylating said second dialkylnaphthalene fraction produced in step II and recycling the product of dealkylation to step I;

III. dealkylating said fraction comprising remaining products of step I and recycling a product of dealkylation to step I;

IV. alkylating said fractions comprising naphthalene and comprising monoalkynaphthalene of step I.

25. A process for producing 2,6-dialkylnaphthalene from a feedstock, comprising the following steps:

I. separating said feedstock into a fraction comprising naphthalene, a fraction comprising monoalkynaphthalene and a fraction comprising dialkylnaphthalene;

II. separating and purifying 2,6-dialkylnaphthalene from said dialkylnaphthalene fraction of step I to produce 2,6-dialkylnaphthalene and a second dialkylnaphthalene fraction;

III. dealkylating said second dialkylnaphthalene fraction produced in step II;

IIIa. recycling the product of step III to step I; and

IV. alkylating said fractions comprising naphthalene and comprising monoalkynaphthalene of step I.

26. A process for producing 2,6-dialkylnaphthalene from a feedstock, comprising the following steps:

I. separating said feedstock into a fraction comprising naphthalene, a fraction comprising monoalkynaphthalene, a fraction comprising dialkylnaphthalene and a fraction lean in dialkylnaphthalene;

II. separating and purifying 2,6-dialkylnaphthalene from said dialkylnaphthalene fraction of step I to produce 2,6-dialkylnaphthalene and a second dialkylnaphthalene fraction;

IIa. isomerizing said fraction lean in dialkylnaphthalene of step I;

IIb. separating the isomerization product of step IIa into a fraction comprising dialkylnaphthalene and a fraction lean in dialkylnaphthalene;

IIc. recycling a dialkylnaphthalene fraction of step IIb to step II;

III. dealkylating said second dialkylnaphthalene fraction produced in step II and a fraction lean in dialkylnaphthalene of step IIb;

IV. alkylating said fractions comprising naphthalene and comprising monoalkylnaphthalene of step I; and V. recycling a product from step III to step I.

27. A process for producing 2,6-dialkylnaphthalene from a feedstock, comprising the following steps:

I. separating said feedstock, in distillation towers, into a fraction comprising 2,6-dimethylnaphthalene, a fraction comprising 1,6-dimethylnaphthalene and a fraction comprising a remainder;

II. purifying 2,6-dialkylnaphthalene from said 2,6-dimethylnaphthlane fraction of step I to produce 2,6-dialkylnaphthalene and a second dialkylnaphthalene fraction;

IIa. isomerizing said 1,6-dimethylnaphthalene fraction of step I;

IIb. separating the isomerization product of step IIa into a fraction comprising 2,6-dimethylnaphthalene and a fraction comprising a remainder;

IIc. feeding said fraction comprising 2,6-dimethylnaphthalene of step IIb to step II;

III. dealkylating said fraction comprising a remainder of step I, said second dialkylnaphthalene fraction produced in step II, and a fraction comprising a remainder of step IIb;

IV. separating a naphthalene and methylnaphthalene fraction from said dealkylation of step III;

V. alkylating said naphthalene and methylnaphthalene fraction of step IV; and

VI. recycling a product from step V to step I.

* * * * *